United States Patent [19]

Warriner

[11] Plant 4,019

[45] Mar. 1, 1977

[54] ROSE PLANT

[75] Inventor: William A. Warriner, Tustin, Calif.

[73] Assignee: Jackson & Perkins Co., Medford, Oreg.

[21] Appl. No.: 650,913

[22] Filed: Jan. 21, 1976

[51] Int. Cl.[2] ..... A01H 5/00

[52] U.S. Cl. ..... Plt./14

[58] Field of Search ..... Plt./14

*Primary Examiner*—Robert E. Bagwill

*Attorney, Agent, or Firm*—Klarquist, Sparkman, Campbell, Leigh, Hall & Whinston

EXEMPLARY CLAIM

1. A new and distinct cultivar of rose plant of the hybrid tea class, substantially as herein shown and described, characterized particularly as to novelty by the unique combination of a vigorous, upright habit of growth, stiff, straight, strong stems, particularly suitable for use as a greenhouse grown cut flower, Garnet Brown new foliage, white to near white (very light Chartreuse Green) buds and open blooms, very light musky fragrance.

1 Drawing Figure

The present invention relates to a new and distinct cultivar of rose plant of the hybrid tea class, which was originated by me by crossing two unnamed cultivars of roses.

The primary objective of this breeding was to produce a cultivar particularly suitable for production of cut flowers in greenhouse culture, having long stems and white buds and open flowers. This objective was fully achieved along with other distinctions as evidenced by the following unique combination of characteristics which are outstanding in this new cultivar and which distinguish it from its parents as well as from all other cultivars of which I am aware:

1. A vigorous habit of growth.
2. Stems grow in a very vertical position, seldom deviating from the vertical, thereby producing straight cutting stems.
3. Strong peduncles that remain stiff when cut as cut flowers.
4. Very pronounced Garnet Brown (W) coloring in new foliage. The undersides of old foliage diaplay an overlay or reddish cast.
5. Nearly white bud and open flower.
6. A slight, musky fragrance.

Asexual reproduction of this new cultivar by budding, as performed at Wasco, Calif., shows that the herein described characteristics and distinctions come true to form and are established and transmitted through succeeding propagations.

The accompanying illustration shows typical specimens of the vegetative growth and flowers of the new cultivar in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed Parent.*—Unnamed cultivar.

*Pollen Parent.*—Unnamed cultivar.

Classification:

*Botanical.*—Rosa hybrid.

*Commercial.*—Hybrid Tea.

FLOWER

Observations made from specimens grown in a greenhouse at Irvine, Calif., December, 1975.

Blooming habit: Continuous.

Bud:

*Size.*—1" to 1¼" when petals start to unfurl.

*Form.*—Pointed ovoid.

*Color.*—When sepals first divide — Chartreuse Green (663/3); when half blown; upper side of petals — near white; lower side of petals — near white.

*Sepals.*—Color: Outer surface slightly lighter than Scheeles Green (860/3) with a slight overcast of Garnet Brown (00918/3) on a few sepals. Inner surface slightly lighter than Scheeles Green (860/3) with some covering of white tomentum. Three appendaged sepals normally appendaged. Two unappendaged sepals hairy edged.

*Receptacle.*—Color: Near Scheeles Green (860/3). Shape: funnel. Size: broad top, medium in size. Surface: smooth.

*Peduncle.*—Length: long. Surface: very slightly prickly. Color: light green. Strength: stiff, erect and slender.

*Opening.*—Outer petals curl on sides, causing the petals to appear pointed in form. Center petals only slightly curled under when fully open.

Bloom:

*Size.*—Large. Average open size is 4" to 4½".

*Borne.*—Singly or several together.

*Stems.*—Long.

*Form.*—When first open — high centered. Permanence — outer petals curl to a point.

*Petalage.*—Number of petals under normal conditions, approximately 27 to 30

*Color.*—Center of flower: Upper side of petals — between white and Chartreuse Green (663/3). Reverse side of petals — near white. Base of petals — from Chartreuse Green (663/1) at point of attachment grading outwardly to Chartreuse Green (663/3). General tonality from a distance — white.

*Discoloration.*—General tonality at end of third day — no change.

*Fragrance.*—Slight.

Petals:

*Texture.*—Thin, soft.

*Shape.*—Round.

*Form.*—Inner petals, tips slightly recurved; outer petals, edges slightly quilled.

*Arrangement.*—Loosely imbricated. Petaloids in center, few.

*Persistence.*—Drop off cleanly.

*Lastingness.*—On the plant — very long. As cut flower — very long.

Reproductive parts:

*Anthers.*—Medium. Color — yellow. Arrangement — regular around styles.

*Filaments.*—Color — dresden yellow (64/2)

*Pollen.*—Light Yellow.

*Styles.*—Color — lower half near white, outer portion Cardinal Red (822/3).

*Stigmas.*—Color — near white.

PLANT

Form: Bush.

Growth: Very vigorous, upright, branching

Foliage: Number of leaflets on normal midstem leaves, 5, occasionally 7.

*Size.*—Large.

*Quantity.*—Normal.

*Color.*—New foliage: Garnet Brown (00918/3). Old foliage: near Spinach Green (0960).

*Shape.*—Oval pointed.

*Texture.*—Upper side: leathery.

*Edge.*—Serrated, undulated.

*Serration.*—Single, small.

*Petiole—(rachis).*—Color: green. Underside: prickles.

*Stipules.*—Long.

*Disease Resistance.*—Normal resistance to mildew under normal growing conditions at Irvine, Calif.

Wood:

*New Wood.*—Color — Garnet Brown (00918/3). Bark — smooth.

*Old Wood.*—Color — Green. Bark — smooth.

Prickles:

*Quantity.*—On main stalks from base — ordinary. On laterals from stalk — ordinary.

*Form.*—Narrow base; long, slightly hooked downward.

*Color When Young.*—Red.

*Position.*—Irregular.

Small Prickles:

*Quantity.*—On main stalks: none. On laterals: none.

*Color.*—none.

I claim:

1. A new and distinct cultivar of rose plant of the hybrid tea class, substantially as herein shown and described, characterized particularly as to novelty by the unique combination of a vigorous, upright habit of growth, stiff, straight, strong stems, particularly suitable for use as a greenhouse grown cut flower, Garnet Brown new foliage, white to near white (very light Chartreuse Green) buds and open blooms, very light musky fragrance.

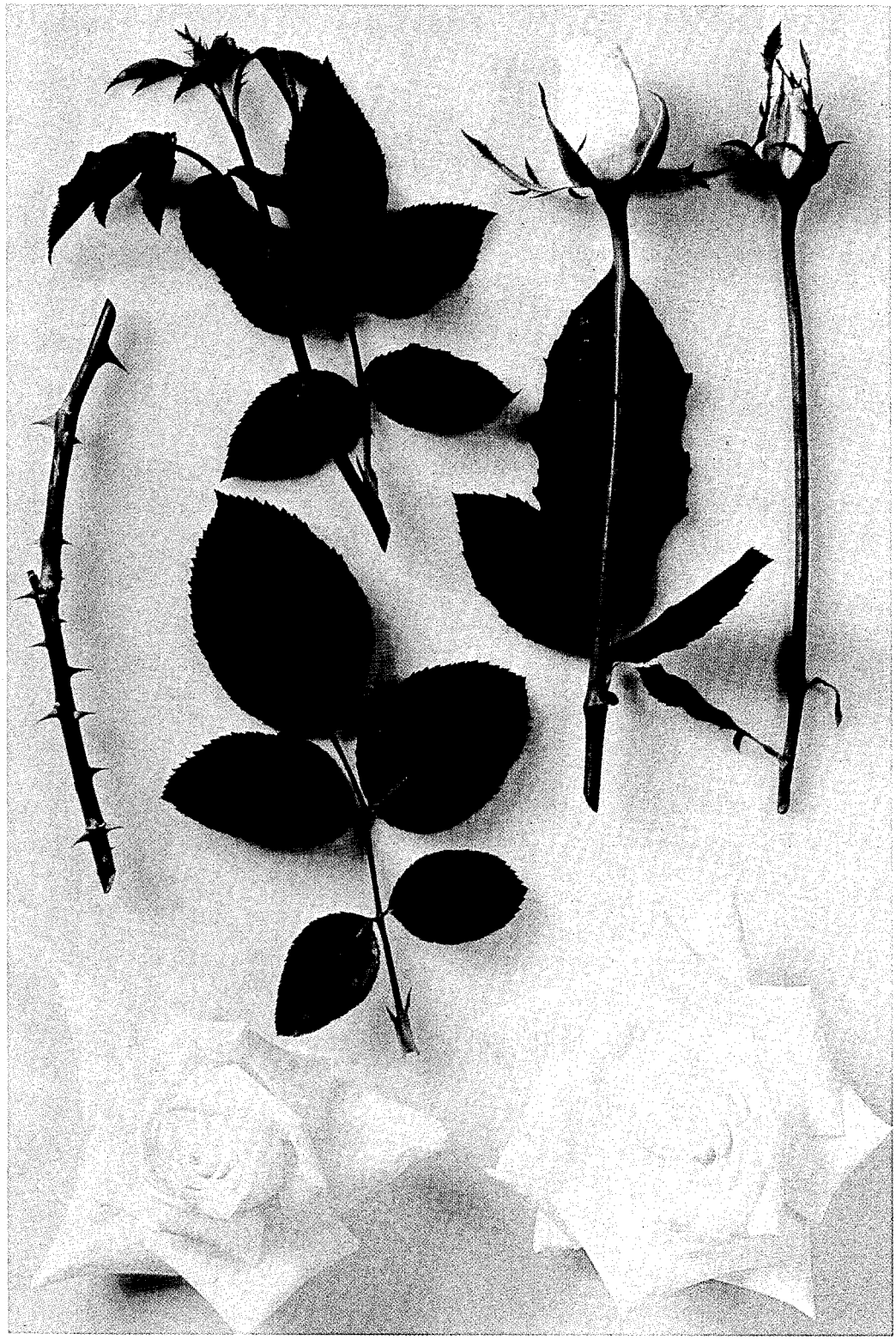

* * * * *